US008955528B1

(12) United States Patent
Escobar et al.

(10) Patent No.: US 8,955,528 B1
(45) Date of Patent: Feb. 17, 2015

(54) DENTURE CLEANING SET

(71) Applicants: Guillermo Escobar, Kissimmee, FL (US); Jorge Leonardo Valderrama, Orlando, FL (US)

(72) Inventors: Guillermo Escobar, Kissimmee, FL (US); Jorge Leonardo Valderrama, Orlando, FL (US)

( * ) Notice: Subject to any disclaimer, the term of this patent is extended or adjusted under 35 U.S.C. 154(b) by 0 days.

(21) Appl. No.: 14/320,571

(22) Filed: Jun. 30, 2014

Related U.S. Application Data

(60) Provisional application No. 61/919,644, filed on Dec. 20, 2013.

(51) Int. Cl.
*A45D 44/18* (2006.01)
*A47K 1/09* (2006.01)
*A61Q 11/00* (2006.01)
*A61K 8/04* (2006.01)
*A46B 9/04* (2006.01)
*A61Q 11/02* (2006.01)

(52) U.S. Cl.
CPC . *A61K 8/044* (2013.01); *A46B 9/04* (2013.01); *A46B 9/045* (2013.01); *A61Q 11/02* (2013.01); *A46B 2200/1073* (2013.01)
USPC .............................. 132/310; 132/308; 424/54

(58) Field of Classification Search
CPC .................................... A46B 9/04; A46B 5/02
USPC ........... 15/167.1, 143.1; 206/570; 424/49, 54; 132/308, 309
See application file for complete search history.

(56) References Cited

U.S. PATENT DOCUMENTS

| 2,236,034 | A | * | 3/1941 | Luce et al. | 15/167.1 |
|---|---|---|---|---|---|
| 2,236,828 | A | * | 4/1941 | Munele | 424/56 |
| 3,839,213 | A | * | 10/1974 | Hill | 510/116 |
| 3,839,552 | A | * | 10/1974 | Kosti | 424/54 |
| 4,828,113 | A | * | 5/1989 | Friedland et al. | 206/570 |
| 5,383,244 | A | * | 1/1995 | Ahrens et al. | 15/106 |
| 5,465,449 | A | * | 11/1995 | Lewkowicz | 15/106 |
| 5,660,546 | A | * | 8/1997 | Shafer | 433/216 |
| 5,881,421 | A | * | 3/1999 | Ducharme | 15/106 |
| 5,920,941 | A | | 7/1999 | Iannotta | |
| 6,121,213 | A | | 9/2000 | Vergara et al. | |
| 6,124,374 | A | | 9/2000 | Kolias et al. | |
| 6,500,406 | B1 | * | 12/2002 | Rajaiah et al. | 424/49 |
| D489,533 | S | * | 5/2004 | Yost et al. | D4/106 |
| 7,258,878 | B2 | | 8/2007 | Greene et al. | |
| 7,458,464 | B1 | * | 12/2008 | Kutsch et al. | 206/570 |
| 7,700,133 | B2 | | 4/2010 | Cooley et al. | |
| 8,464,388 | B2 | * | 6/2013 | Chen | 15/106 |
| 8,518,381 | B2 | * | 8/2013 | LeBlanc et al. | 424/49 |
| 8,623,388 | B2 | * | 1/2014 | Rajaiah et al. | 424/401 |
| 2009/0246151 | A1 | * | 10/2009 | LeBlanc et al. | 424/49 |
| 2011/0217246 | A1 | * | 9/2011 | Deng et al. | 424/49 |

FOREIGN PATENT DOCUMENTS

DE          19927708 A1 * 12/2000

* cited by examiner

*Primary Examiner* — Robyn Doan
(74) *Attorney, Agent, or Firm* — KB Patents; Luca D'Ottone

(57) ABSTRACT

The instant application is an all-natural denture cream designed to remove stains, clean, disinfect, and shine the denture with minimal effort within seconds There is also an added double headed brush that can be used with the cream, with a curved easy grip feature that will allow for easy cleaning experience. The brush is designed to reach those hard to access spots of the denture that could not be otherwise accessed by the fingers alone.

5 Claims, 4 Drawing Sheets

DENTURE CLEANING SET

CLAIM OF PRIORITY FROM RELATED APPLICATIONS

The present application claims priority from U.S. Provisional Patent Application No. 61/919,644 filed on Dec. 20, 2013 to Guillermo Escobar Kissimmee, (FL) and to Jorge Leonardo Valderrama Orlando, (Fla.), directed to ALADDINE, that is hereby incorporated by reference.

BACKGROUND OF THE INVENTION

1. Field of the Invention

The inventive device described in the instant application is a denture cream that will remove stains, disinfect, and shine the denture just with rubbing. It is designed to be primarily used as a composition to cleans dentures that will be available in a tube form similar to toothpaste tubes. The ALADDINE may be used alone or in combination with water. If used in combination with water it becomes more efficient. This provides a safe and natural alternative for users who use dentures to clean, disinfect, and shine their teeth. There will also be an added double headed brush that can be used with the cream, with a curved easy grip feature that will allow for easy cleaning experience. The brush is specifically designed to reach all places that cannot be reached by fingers.

2. Brief Description of the Prior Art

Denture cleaning devices are well known in the art. Various Patents and Published Patent applications are in fact directed to denture cleaners. While developing the invention of the instant application independently the Inventor researched extensively the public record as well as the current market for denture cleaners and the most relevant examples found in the search are mentioned in the Information Disclosure Statement (IDS) attached.

Despite all the efforts listed above prior art patents describe structures that are either not truly convenient or else involve complicated, expensive, and overly difficult assembly and/or disassembly parts and procedures. Other devices have been advertised on various media but never patented or described into a printed publication.

SUMMARY OF THE INVENTION

The inventive device described in the instant application is an all-natural denture cream whose composition is designed to remove stains, disinfect, and shine the denture just by rubbing. It will be primarily used as a device that will clean dentures that will be available in a tube form similar to toothpaste tubes. This provides a safe and natural alternative for users who use dentures to clean and disinfect their teeth. There will also be an added double headed brush that can be used with the cream, with a curved easy grip feature that will allow for easy cleaning experience. The brush is designed to reach those spots that cannot be accessed by fingers. The mechanism for the invention is a tube of cream that will remove stains, clean, disinfect, and shine dentures with the help of a double-headed brush just by rubbing.

It is then the principal object of the present invention is to provide a cream that will easily remove stains, disinfect, and shine dentures.

It is a secondary objective of the present invention to eliminate the necessity of soaking dentures for long periods of time to clean them.

It is an additional objective of the present invention to provide a device that does not decay or deteriorate over time and that has a long shelf life. It is a final objective of the present invention to provide for a device that is relatively inexpensive to build, but that can eventually be sold at a premium.

These and other objective achieved by the device of the present invention will be apparent by the drawings, by their detailed description, and by the specification here from appended.

DESCRIPTION OF THE PREFERRED EMBODIMENT

Figure 1:
FIG. 1 is a horizontal angled elevation view of one of the preferred embodiments of "Aladdine" in accordance with the teachings of the present invention.
Figure 2:
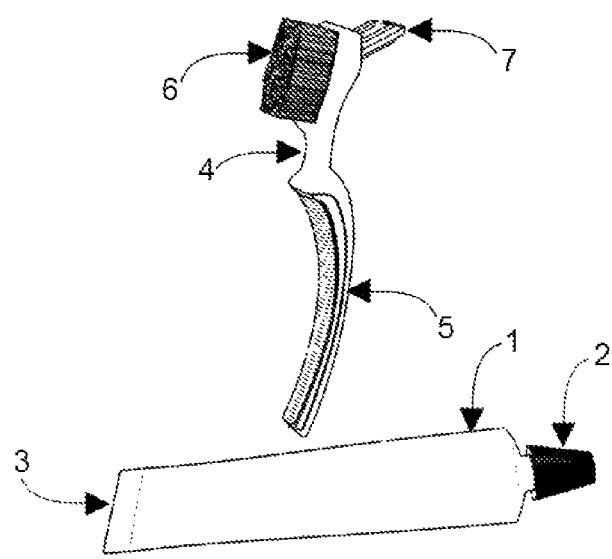
FIG. 2 is a side angled elevation view of "Aladdine" of FIG. 1.
Figure 3:
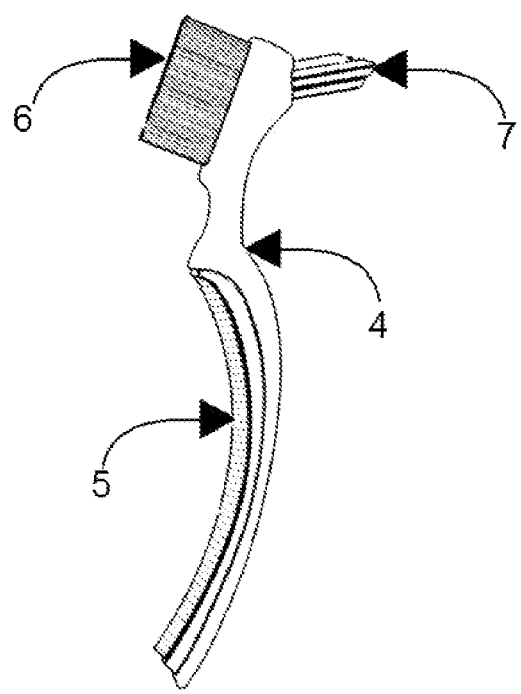
FIG. 3 is a side elevation view of "Aladdine" of the brush of FIG. 2.
Figure 4:
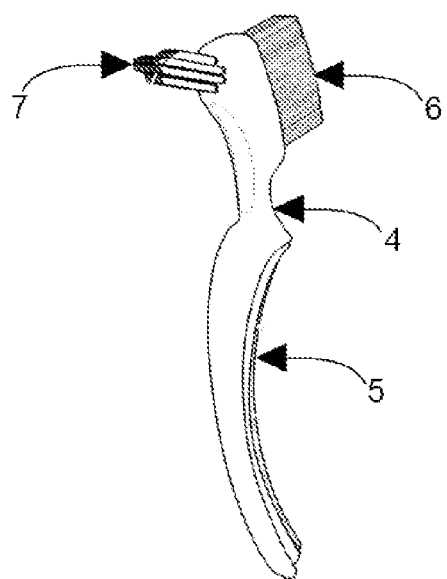
FIG. 4 is a backside angled elevation view of "Aladdine" of the brush of FIG. 2.

The inventive device described in the instant application is an all-natural denture cream that will remove stains, disinfect, and shine the denture just with rubbing. It will be primarily used as a device that will clean dentures that will be available in a tube form similar to toothpaste tubes. This provides a safe and natural alternative for users who use dentures to clean and disinfect their teeth.

There will also be an added double headed brush that can be used with the cream, with a curved easy grip feature that will allow for easy cleaning experience. The brush is especially designed to reach those hard to access spots that cannot be accessed with the fingers. The mechanism for the invention is a tube of cream that will remove stains and clean dentures with the help of a double-headed brush. As it can be inferred from the drawings essential components of the "Aladdine" of the present application include: tube of cream, cap, grip, handle, bristles, and rubber brush.

The Alladine are designed as a cream to easily disinfect, remove stains, and shine dentures with the use of a brush to scrub the dentures. Essential components of the cream of the present invention include: baking soda, powdered pumice stone, and mineral oil. In one preferred embodiment of "Aladdine" the cream is made by mixing approximately 6 ounces of baking soda, with 1 ounce of powdered pumice stone, into 5 ounces of mineral oil. Use of this product will eliminate the need to soak dentures overnight or to spend an inordinate amount of time scrubbing the dentures with a brush and other kinds of cleaning products.

The premise is to have the ability to use a cream rather than soaking the dentures to remove stains and plaque from them. This device will also eliminate the need to wear unattractive dentures which are stained.

Users can then use the dentures with confidence that the cream has done its job. The "Aladdine" provides an easy way to remove stains and plaque from dentures with the help of a double-headed brush.

With the exact formulaic composition of the cream there are two kind of ounces: fluid ounces liquid used to each fluid ounce=28.41 mL and the others are regular (weight) ounces equal 28.35 grams. If we take this into consideration the final mixture composition is: Baking Soda: 6 oz×28.35 grams=170.1 grams; Pumice Stone 1 oz×28.35 grams=28.35 grams; Mineral Oil: 5 oz fluid×28.41 mL=142.05 mL. Washing soda or potassium carbonate or potassium bicarbonate may be substituted in a one to one ratio with the baking soda because of their similar chemical properties.

Dentures, also known as false teeth, are prosthetic devices constructed to replace missing teeth; they are supported by the surrounding soft and hard tissues of the oral cavity. Conventional dentures are removable. However, there are many different denture designs, some which rely on bonding or clasping onto teeth or dental implants. There are two main categories of dentures, the distinction being whether they are used to replace missing teeth on the mandibular arch or on the maxillary arch.

Toothpaste is a paste or gel dentifrice used with a toothbrush as an accessory to clean and maintain the aesthetics and health of teeth. Toothpaste is used to promote oral hygiene: it serves as an abrasive that aids in removing the dental plaque and food from the teeth, assists in suppressing halitosis, and delivers active ingredients (most commonly fluoride) to help prevent tooth and gum disease.

In one of its preferred embodiments the inventive device of the present application embodies an organic all natural cream to clean and remove stains comprises: The tube of cream (1), with a sealable plastic cap (2) and a malleable strip (3) to coil the tube to squeeze out the remaining cream. There is also the included brush (4) with a conforming grip (5) to be used with the coarse bristles (6) and the rubber brush (7) to get a deep clean.

A mineral oil is any of various colorless, odorless, light mixtures of alkanes in the C15 to C40 range from a non-vegetable (mineral) source, particularly a distillate of petroleum. The name mineral oil has been used to label many specific oils over the past few centuries. Other names, similarly imprecise, include white oil, liquid paraffin, pariffinum liquidum, and liquid petroleum. Baby oil refers to a perfumed mineral oil.

Most often, mineral oil is a liquid by-product of the distillation of petroleum to produce gasoline and other petroleum-based products from crude oil. A mineral oil in this sense is a transparent, colorless oil composed mainly of alkanes and cyclic paraffins, related to petroleum jelly (also known as "white petrolatum"). It has a density of around 0.8 g/cm$^3$. Mineral oil is a substance of relatively low value, and it is produced in very large quantities. Mineral oil is available in light and heavy grades, and can often be found in drug stores. There are three basic classes of refined mineral oils: paraffinic oils, based on n-alkanes; naphthenic oils, based on cycloalkanes; aromatic oils, based on aromatic hydrocarbons.

Mineral oil is a common ingredient in baby lotions, cold creams, ointments and cosmetics. It is a lightweight inexpensive oil that is odorless and tasteless. It can be used on eyelashes to prevent brittleness and breaking and, in cold cream, is also used to remove creme make-up and temporary tattoos. One of the common concerns regarding the use of mineral oil is its presence on several lists of comedogenic substances. These lists of comedogenic substances were developed many years ago and are frequently quoted in the dermatological literature.

Food grade mineral oil has an E number of E905a, although it is not approved in food products in the European Union, and incidental amounts in foods are carefully regulated. Because of its properties that prevent water absorption, combined with its lack of flavor and odor, food grade mineral oil is a popular preservative for wooden cutting boards, salad bowls and utensils. Rubbing a small amount of mineral oil into a wooden kitchen item periodically will prevent absorption of food odors and ease cleaning, as well as maintain the integrity of the wood, which is otherwise subjected to repeated wetting and drying in the course of use. The oil fills small surface cracks that may otherwise harbor bacteria.

Outside of the European Union, it is occasionally used in the food industry, particularly for candy. In this application, it is typically used for the glossy effect it produces, and to prevent the candy pieces from adhering to each other. It has been discouraged for use in children's foods, though it is still found in many candies, including Swedish Fish. The use of food grade mineral oil is self-limiting because of its laxative effect. The maximum daily intake is calculated to be about 100 mg, of which some 80 mg are contributed from its use on machines in the baking industry.

Mineral oil it is sometimes used as a lubricant in enema preparations, because most of the ingested material is excreted in the stool rather than being absorbed by the body.

Sodium bicarbonate or sodium hydrogen carbonate is the chemical compound with the formula $NaHCO_3$. Sodium bicarbonate is a white solid that is crystalline but often appears as a fine powder. It has a slightly salty, alkaline taste resembling that of washing soda (sodium carbonate). The natural mineral form is nahcolite. It is a component of the mineral natron and is found dissolved in many mineral springs. It is among the food additives encoded by European Union, identified by the initials E 500. Since it has long been known and is widely used, the salt has many related names such as baking soda, bread soda, cooking soda, and bicarbonate of soda. In colloquial usage, its name is sometimes shortened to sodium bicarb, bicarb soda, simply bicarb, or even bica. The word saleratus, from Latin sal æratus meaning aerated salt, was widely used in the 19th century for both sodium bicarbonate and potassium bicarbonate. The term has now fallen out of common usage. Sodium bicarbonate is usually called baking soda in general terms.

Sodium bicarbonate, referred to as "baking soda" is primarily used in cooking (baking), as a leavening agent. It reacts with acidic components in batters, releasing carbon dioxide, which causes expansion of the batter and forms the characteristic texture and grain in pancakes, cakes, quick breads, soda bread, and other baked and fried foods. Acidic compounds that induce this reaction include phosphates, cream of tartar, lemon juice, yogurt, buttermilk, cocoa, vinegar, etc.

Sodium bicarbonate can be substituted for baking powder provided sufficient acid reagent is also added to the recipe. Many forms of baking powder contain sodium bicarbonate combined with calcium acid phosphate, sodium aluminum sulphate or cream of tartar.

Sodium bicarbonate was sometimes used in cooking vegetables, to make them softer, although this has gone out of fashion, as most people now prefer firmer vegetables. However, it is still used in Asian and Latin American cuisine to tenderise meats. Baking soda may react with acids in food, including Vitamin C (L-ascorbic acid). It is also used in breadings such as for fried foods to enhance crispness.

Heat causes sodium bicarbonate to act as a raising agent by releasing carbon dioxide when used in baking. The carbon dioxide production starts at temperatures above 80° C. Since the reaction does not occur at room temperature, mixtures (cake batter, etc.) can be allowed to stand without rising until they are heated in the oven.

A paste from baking soda can be very effective when used in cleaning and scrubbing. For cleaning aluminium objects, the use of sodium bicarbonate is discouraged as it attacks the thin unreactive protective oxide layer of this otherwise very reactive metal. A solution in warm water will remove the tarnish from silver when the silver is in contact with a piece of aluminium foil. A paste of sodium bicarbonate and water is useful in removing surface rust as the rust forms a water soluble compound when in a concentrated alkaline solution. Cold water should be used as hot water solutions can corrode steel.

Baking soda is commonly added to washing machines as a replacement for softener and to remove odors from clothes. Sodium bicarbonate is also effective in removing heavy tea and coffee stains from cups when diluted with warm water.

Pumice called pumicite in its powdered or dust form, is a volcanic rock that consists of highly vesicular rough textured volcanic glass, which may or may not contain crystals. It is typically light colored. Scoria is another vesicular volcanic rock that differs from pumice in having larger vesicles and thicker vesicle walls and being dark colored and denser. Under the teachings of the present application an amount of grinded scoria may be substituted in a one to one to the amount of grinded pumice stone.

Pumice is created when super-heated, highly pressurized rock is violently ejected from a volcano. The unusual foamy configuration of pumice happens because of simultaneous rapid cooling and rapid depressurization. The depressurization creates bubbles by lowering the solubility of gases (including water and $CO_2$) that are dissolved in the lava, causing the gases to rapidly exsolve (like the bubbles of $CO_2$ that appear when a carbonated drink is opened). The simultaneous cooling and depressurization freezes the bubbles in the matrix. Eruptions underwater are rapidly cooled and the large volume of pumice created can be a shipping hazard.

Pumice is widely used to make lightweight concrete or insulative low-density cinder blocks. When used as an additive for cement, a fine-grained version of pumice called pozzolan is mixed with lime to form a light-weight, smooth, plaster-like concrete. This form of concrete was used as far back as Roman times. Roman engineers used it to build the huge dome of the Pantheon and as construction material for many aqueducts.

It is also used as an abrasive, especially in polishes, pencil erasers, cosmetic exfoliants, and the production of stone-washed jeans. "Pumice stones" are often used in beauty salons during the pedicure process to remove dry and excess skin from the bottom of the foot as well as calluses. It was also used in ancient Greek and Roman times to remove excess hair. Finely ground pumice is added to some toothpastes and heavy-duty hand cleaners (such as Lava soap) as a mild abrasive. Pumice is also used as a growing substrate for growing horticultural crops. Some brands of chinchilla dust bath are made of powdered pumice.

Owing to its high demand particularly for water filtration, chemical spill containment, cement manufacturing, horticulture and increasingly for the pet industry, mining of pumice in environmentally sensitive areas have been under more scrutiny after such an operation was stopped in the U.S. state of Oregon, at Rock Mesa in the southern part of the Three Sisters Wilderness.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A denture cleaning assembly comprising:
   a) a tube holding denture cream, said tube including a sealable plastic twist on cap and a malleable strip to coil the tube; wherein said denture cream consisting of 170.1 g of baking soda, 28.35 g of grinded pumice stone and 142.05 ml of mineral oil; the mineral oil being selected from one of the following groups of light mixtures of alkanes in the C15 to C40 range from a non-vegetable source, a distillate of petroleum, a paraffinic oil based on n-alkanes, naphthenic oil based on cycloalkanes, aromatic oil based on aromatic hydrocarbons;
   b) a double headed brush including a front brush having coarse bristles for scrubbing and a rubber brush on a backside of said front brush for deep cleaning; a curved easy grip extending from one end of said brush.

2. The denture cleaning assembly of claim 1 where said baking soda is nahcolite.

3. The denture cleaning assembly of claim 1 further comprising a physiological cooling compound.

4. The denture cleaning assembly of claim 3 where said physiological cooling compound is menthol.

5. The denture cleaning assembly of claim 1 where said denture cream can be used with water.

* * * * *